(12) United States Patent
Wang

(10) Patent No.: US 12,016,555 B2
(45) Date of Patent: Jun. 25, 2024

(54) METHOD OF FORMING AN ANVIL FOR A SURGICAL STAPLER

(71) Applicant: Cilag GmbH international, Zug (CH)

(72) Inventor: Bingshi Wang, Mason, OH (US)

(73) Assignee: Cilag GmbH International, Zug (CH)

( * ) Notice: Subject to any disclaimer, the term of this patent is extended or adjusted under 35 U.S.C. 154(b) by 496 days.

(21) Appl. No.: 17/093,704

(22) Filed: Nov. 10, 2020

(65) Prior Publication Data

US 2022/0142641 A1 May 12, 2022

(51) Int. Cl.
| | |
|---|---|
| *B21D 22/02* | (2006.01) |
| *A61B 17/068* | (2006.01) |
| *A61B 17/072* | (2006.01) |
| *B21D 13/02* | (2006.01) |
| *B23P 11/00* | (2006.01) |
| *B23P 15/00* | (2006.01) |

(52) U.S. Cl.
CPC ........ *A61B 17/0686* (2013.01); *A61B 17/072* (2013.01); *B21D 13/02* (2013.01); *B23P 11/00* (2013.01); *B23P 15/00* (2013.01); *A61B 2017/07264* (2013.01); *B21D 22/02* (2013.01)

(58) Field of Classification Search
CPC ...................................................... B21D 13/02
See application file for complete search history.

(56) References Cited

U.S. PATENT DOCUMENTS

| | | | | |
|---|---|---|---|---|
| 6,953,138 | B1 * | 10/2005 | Dworak | ........... A61B 17/07207 227/181.1 |
| 7,086,267 | B2 * | 8/2006 | Dworak | ........... A61B 17/07207 72/413 |
| 7,762,445 | B2 * | 7/2010 | Heinrich | .......... A61B 17/07207 606/8 |
| 9,662,700 | B2 * | 5/2017 | Taguchi | .............. H01M 8/0206 |
| 9,962,751 | B2 * | 5/2018 | Hirata | .................... B21D 13/02 |
| 10,709,452 | B2 | 7/2020 | DiNardo et al. | |
| 10,898,187 | B2 | 1/2021 | Deck et al. | |
| 11,033,266 | B2 | 6/2021 | Jones et al. | |
| 11,051,819 | B2 | 7/2021 | Bakos et al. | |
| 11,202,628 | B2 | 12/2021 | Posey et al. | |
| 2009/0261145 | A1 | 10/2009 | Heinrich et al. | |
| 2012/0080492 | A1 | 4/2012 | Scirica et al. | |

(Continued)

OTHER PUBLICATIONS

International Search Report and Written Opinion dated Feb. 8, 2022 for Application No. PCT/IB2021/060304, 12 pgs.

*Primary Examiner* — Sarang Afzali
(74) *Attorney, Agent, or Firm* — Frost Brown Todd LLP

(57) ABSTRACT

A method is provided for forming a surgical stapler anvil with a first punch having a first plurality of protrusions and an opposing second punch having a second plurality of protrusions. A workpiece having first and second sides is positioned between the first and second punches. The first side is contacted by the first punch, thereby plastically deforming the first side with the first plurality of protrusions to displace material of the first side toward the second side. The second side is contacted by the second punch, thereby plastically deforming the second side to displace material of the second side toward the first side. A plurality of pockets is formed in the first side via the contact of the first punch with the first side and the contact of the second punch with the second side. Each of the pockets is configured to deform a leg of a surgical staple.

14 Claims, 10 Drawing Sheets

(56) References Cited

U.S. PATENT DOCUMENTS

| | | |
|---|---|---|
| 2020/0046353 A1 | 2/2020 | Deck et al. |
| 2020/0113561 A1 | 4/2020 | Schings et al. |
| 2020/0237368 A1 | 7/2020 | Bruns et al. |
| 2020/0337698 A1 | 10/2020 | Simms |
| 2021/0038223 A1 | 2/2021 | Schings et al. |

* cited by examiner

METHOD OF FORMING AN ANVIL FOR A SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components and methods have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
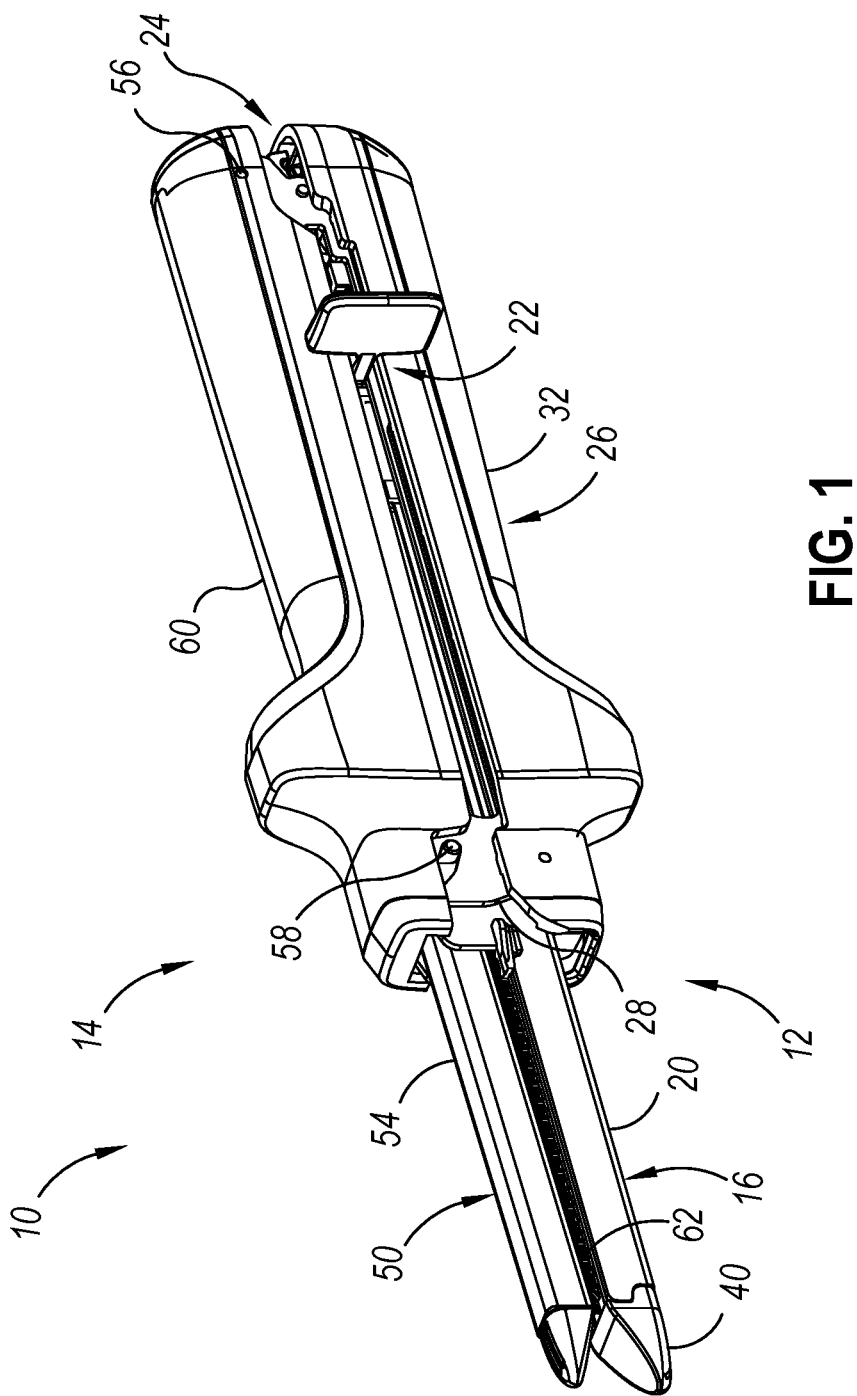
FIG. 1 depicts a perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

Figure 2:
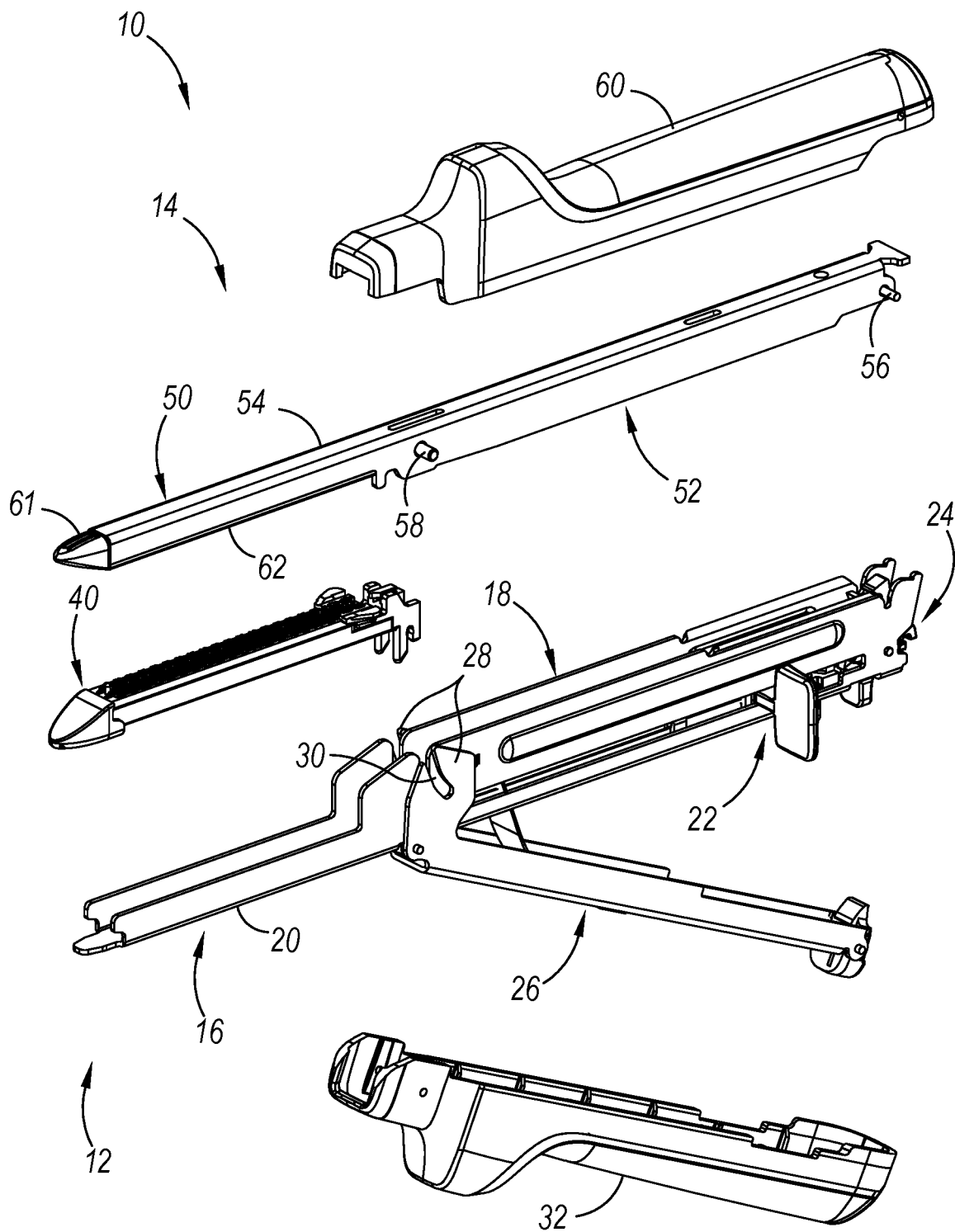
FIG. 2 depicts an exploded perspective view of the linear surgical stapler of FIG. 1.

FIGS. 1-2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) of linear surgical stapler (10) includes an elongate cartridge channel (16) having a proximal frame portion (18) and a distal jaw portion (20). Proximal frame portion (18) slidably retains a firing assembly (22) and includes a proximal retaining assembly (24) configured to releasably retain firing assembly (22) and a proximal coupling pin (56) of anvil half (14). Distal jaw portion (20) is configured to receive a staple cartridge (40) (or "reload"), which houses a plurality of staples (not shown).

Cartridge half (12) further includes a clamp lever (26) (also referred to as a "latch lever") pivotably coupled to cartridge channel (16) and having a pair of opposed jaws (28) that extend distally. Each jaw (28) includes a slot (30) having a closed proximal end and an open distal end configured to receive a distal latch pin (58) of anvil half (14), as described below. Clamp lever (26) is operable to pivot relative to cartridge channel (16) from an open position (see FIG. 2) to a closed position (see FIG. 1) to capture latch pin (58) within clamp lever jaw slots (30) and thereby clamp anvil half (14) against cartridge half (12) for clamping tissue between staple cartridge (40) and an anvil plate (62) of anvil half (14). In the present version, a clamp lever shroud (32) is affixed to an outwardly facing side of clamp lever (26).

Anvil half (14) of linear surgical stapler (10) includes an elongate anvil channel (50) having a proximal frame portion (52) and a distal jaw portion (54). Proximal frame portion (52) includes proximal coupling pin (56) at a proximal end and distal latch pin (58) at a distal end. Proximal frame portion (52) is configured to be received by proximal frame portion (18) of cartridge channel (16) when stapler halves (12, 14) are coupled together, and an outwardly facing side of proximal frame portion (52) is fitted with an anvil shroud (60) in the present example. Distal jaw portion (54) of anvil channel (50) supports a distal tip insert (61) and an anvil plate (62) configured to receive and deform staples ejected by staple cartridge (40). Distal tip insert (61) may be coupled with distal jaw portion (54) in a variety of suitable manners, such as via distal latch pin (58) or heat staking, for example. Anvil plate (62) may be formed separately from distal jaw portion (54) and then secured relative to distal jaw portion (54). For instance, anvil plate (62) may be welded directly to side flanges of distal jaw portion (54), or alternatively anvil plate (62) may be heat staked to a plastic component (not shown) housed within distal jaw portion (54). Various other methods of securing anvil plate (62) to distal jaw portion (54) will be readily apparent to those of ordinary skill in the art in view of the teachings herein. In other versions, anvil plate (62) may be formed integrally with and as a portion of distal jaw portion (54) such that anvil plate (62) and distal jaw portion (54) are formed as a single unitary piece.

Figure 3:
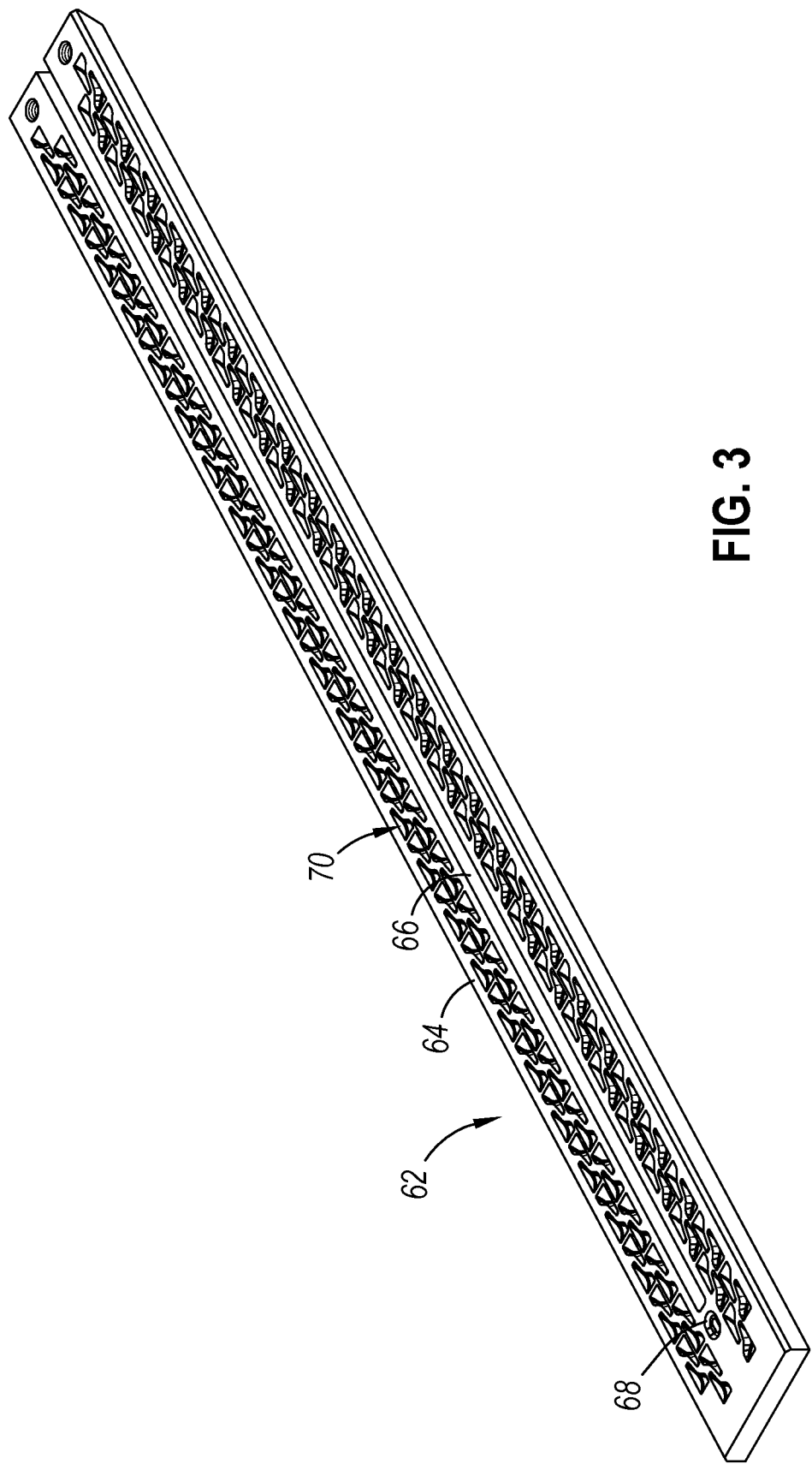
FIG. 3 depicts a perspective view of an anvil plate of the linear surgical stapler of FIG. 1.
Figure 4:
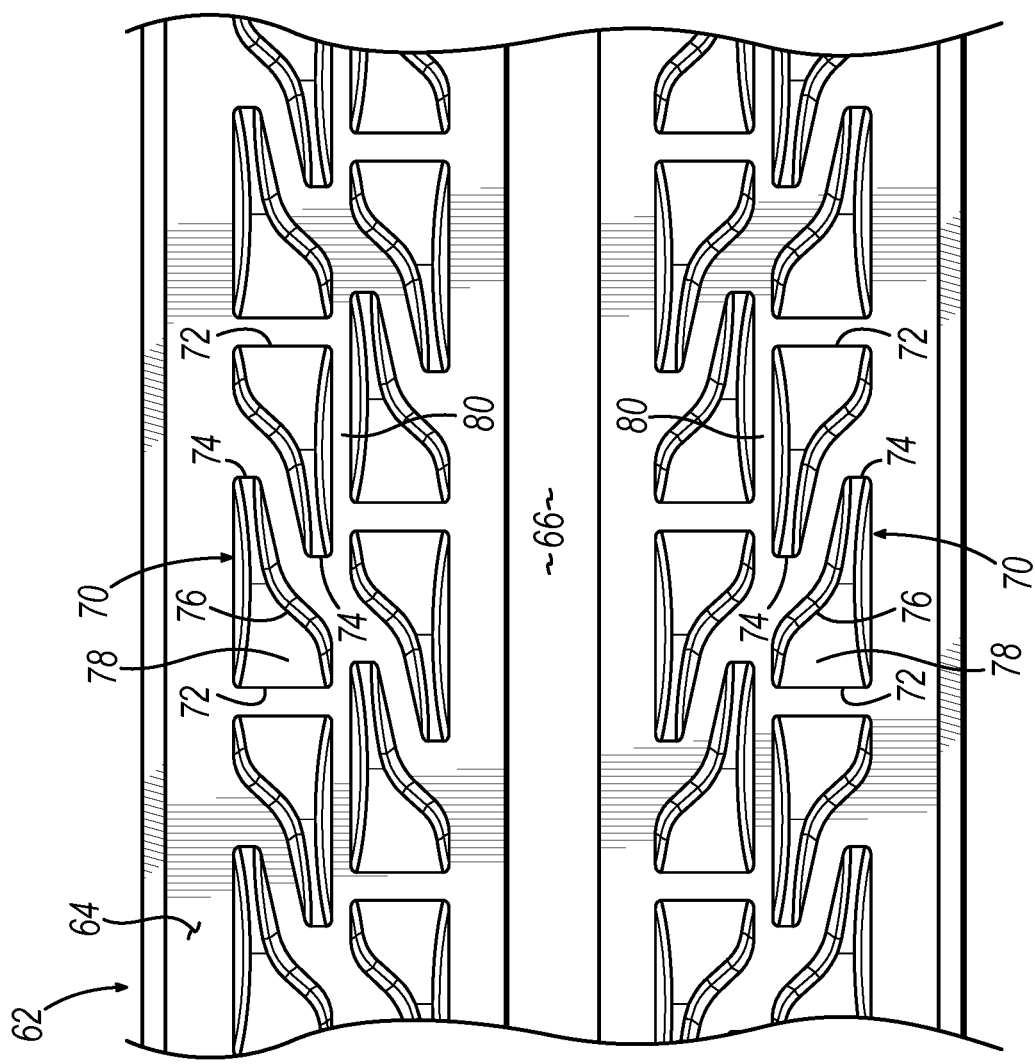
FIG. 4 depicts an enlarged top plan view of a portion of the anvil plate of FIG. 3.

As shown in FIGS. 3 and 4, anvil plate (62) includes an anvil surface (64) and an elongate knife slot (66) that extends longitudinally through anvil surface (64) from a proximal end of anvil plate (62) to a location just proximal to a distal end of anvil plate (62). Knife slot (66) is configured to slidably receive a knife member (not shown) of firing assembly (22) when firing assembly (22) is actuated distally to fire stapler (10). A jaw alignment dimple (68) is formed in anvil surface (64) just distal to and in longitudinal alignment with the distal end of knife slot (66). Jaw alignment dimple (68) is configured to receive a corresponding protrusion formed at the distal end of a deck surface of staple cartridge (40) when staple halves (12, 14) are clamped together. In this manner, jaw alignment dimple (68) is configured to promote lateral alignment of the distal ends of staple cartridge (40) and anvil plate (62) with one another, as well as define a properly sized transverse tissue gap between the distal ends of staple cartridge (40) and anvil plate (62) in the clamped state to thereby promote proper formed staple heights during firing. Jaw alignment dimple (68) may be formed with various suitable shapes, such as various elongate shapes and/or irregular shapes, for example.

Anvil plate (62) further includes a plurality of staple forming pockets (70) that are arranged in pairs on anvil surface (64) on each side of knife slot (66). Each staple forming pocket (70) is configured to receive and deform a respective leg of a staple (not shown) ejected by staple cartridge (40) when stapler (10) is fired. Accordingly, staple forming pockets (70) cooperate to form the ejected staples in tissue clamped between staple cartridge (40) and anvil plate (62). In the present version, anvil plate (62) includes two linear rows of staple forming pockets (70) on each side of knife slot (66), though it will be appreciated that anvil plate (62) may include various other configurations of staple pockets (70) in other versions.

Figure 11:
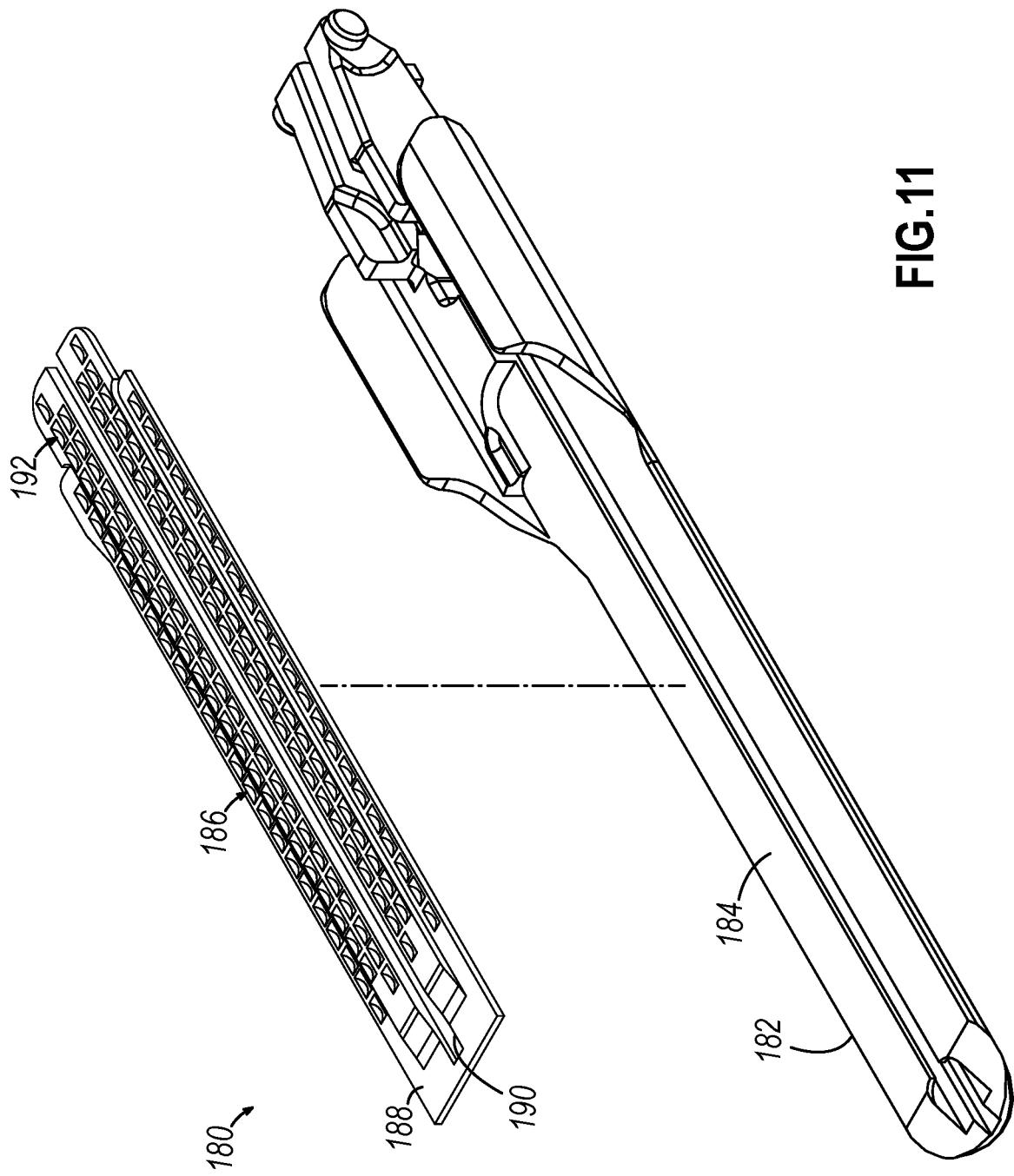
FIG. 11 depicts a disassembled perspective view of an exemplary anvil assembly of another surgical stapler type, showing an anvil plate having pockets formed via a coining method similar to the method shown in FIG. 5.

As shown best in FIG. 4, staple forming pockets (70) are arranged in longitudinally adjacent pairs such that each pair is configured to receive and deform the legs of a respective staple and thereby transform the staple into a formed shape when firing assembly (22) is actuated distally. In the present version, each staple pocket (70) is shaped to provide the resulting staple with a three-dimensional formed shape in which the crown and each bent leg of the formed staple lies in a different plane, for example as disclosed in greater detail in U.S. patent application Ser. No. 16/537,005, entitled "Linear Surgical Stapler," filed on Aug. 9, 2019, issued as U.S. Pat. No. 11,229,433 on Jan. 25, 2022, the disclosure of which is incorporated by reference herein. In other versions, pockets (70) may be alternatively shaped to provide the resulting formed staple with a B-shape in which the crown and each bent leg of the formed staple lies in the same plane, for example as shown in FIG. 11 described below.

As shown in FIG. 4, each individual pocket (70) of the present version includes an entry end (72) having a larger first width and an exit end (74) having a smaller second width, such that pocket (70) has a generally right-triangular shape. A medial portion of each pocket (70) located between entry and exit ends (72, 74) includes an angled sidewall (76) that faces toward entry end (72) and which is longitudinally adjacent to the exit end (74) of an adjacent, longitudinally-paired pocket (70). Each pocket (70) further includes a concave base surface (78) that extends between entry end (72) and exit end (74) such that pocket (70) has a varying depth along its length. Entry end (72) is configured to receive and guide a staple leg in an unformed state longitudinally along concave base surface (78) and toward angled sidewall (76) to be deformed. Exit end (74) is configured to guide the staple leg in a deformed state in a direction toward staple cartridge (40) and into clamped tissue.

Each pair of pockets (70) exhibits reflective symmetry relative to each other such that entry ends (72) of the pair are aligned with yet longitudinally opposed from one another, and such that exit ends (74) of the pair are longitudinally adjacent to yet laterally offset from one another. Additionally, each pocket (70) of a laterally inner row of pockets (70) located adjacent to knife slot (66) is separated from a laterally adjacent pocket (70) in the corresponding outer row of pockets (70) by a longitudinal wall (80). In the present example, longitudinal wall (80) may have a thickness of approximately 0.010 inches or less in a direction transverse to a path of knife slot (66).

In use, the patient tissue to be stapled and cut is positioned between staple cartridge (40) of cartridge half (16) and anvil plate (62) of anvil half (14). Before or after positioning the patient tissue between stapler halves (12, 14), the proximal ends of stapler halves (12, 14) are releasably coupled together by engaging proximal coupling pin (56) of anvil half (14) with proximal retaining assembly (24) of cartridge half (16). Stapler halves (12, 14) are then approximated at their distal ends to direct distal latch pin (58) of anvil half (14) into clamp lever jaw slots (30) of cartridge half (16). Clamp lever (26) is then rotated to the closed position seen in FIG. 1 to clamp anvil half (14) against cartridge half (16), thereby clamping the patient tissue between staple cartridge (40) and anvil plate (62). Firing assembly (22) is then actuated distally by the user to drive the staples housed within staple cartridge (40) through the clamped tissue and against anvil plate (62), and to simultaneously drive a knife (not shown) distally along staple cartridge (40) and anvil plate (62) to thereby cut the clamped tissue. Following completion of this distal firing stroke, firing assembly (22) is retracted proximally and clamp lever (26) is reopened to thereby release the stapled and cut tissue and enable separation of the stapler halves (12, 14).

Linear surgical stapler (10) may be further configured and operable in accordance with any of the teachings of the references incorporated by reference above, as well as U.S. Pat. Pub. No. 2020/0046350, entitled "Firing System for Linear Surgical Stapler," published Feb. 13, 2020; U.S. Pat. Pub. No. 2020/0046351, entitled "Decoupling Mechanism for Linear Surgical Stapler," published Feb. 13, 2020; and/or U.S. Pat. Pub. No. 2020/0046353, entitled "Clamping Assembly for Linear Surgical Stapler," published Feb. 13, 2020, the disclosures of which are incorporated by reference herein.

II. Exemplary Method of Forming Anvil Pockets

Anvil plate (62) of surgical stapler (10) described above may be formed of a surgical grade metal, such as steel, and staple forming pockets (70) may be formed in anvil surface (64) using one or more suitable manufacturing methods. One such method, known as coining, is a form of precision stamping in which a workpiece is struck by a punch with sufficient force to induce plastic flow of material in the workpiece surface. The plastic flow reduces surface grain size and work hardens the surface of the workpiece, while material deeper within the workpiece retains its toughness and ductility. In the present context, anvil plate (62) is initially provided in the form of a flat, elongate rectangular metal blank, which is supported on a stationary structure. A coining punch having a plurality of suitably formed protrusions is then driven against anvil surface (64) with sufficient force to form (i.e., "coin") anvil pockets (70).

In some instances, the use of a single punch for forming anvil pockets (70) with an acceptable degree of precision may require a stamping force (also referred to as "tonnage") that yields tool stresses on the punch that result in an unacceptably short life of the punch and related tooling. The exemplary coining method described below utilizes first and second punches that cooperate with one another to form anvil pockets (70) in anvil surface (64) with superior precision while minimizing the requisite stamping force and resulting tool stresses, and thereby providing an extended tooling life. As will be described below, it will be appreciated that the exemplary method may be employed for forming anvil pockets for a variety of types of stapling mechanisms, some of which are illustrated in the drawings.

Figure 5:
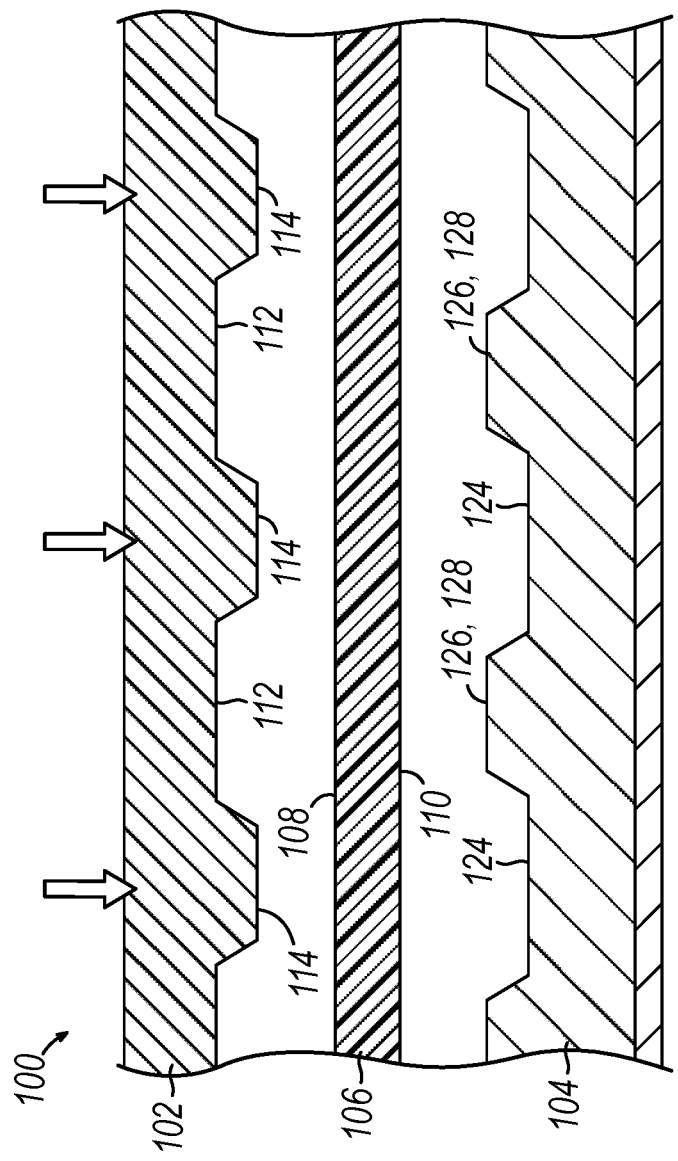
FIG. 5 depicts a schematic side sectional view of an exemplary anvil pocket coining assembly including a pocket-forming top punch, an embossing bottom punch, and a workpiece positioned between the top and bottom punches.

A. Exemplary Coining Assembly Having Pocket-Forming Top Punch and Embossing Bottom Punch FIG. 5 schematically shows an exemplary coining assembly (100) for forming pockets (70) of anvil plate (62). Coining assembly (100) of the present version includes a pocket-forming top punch (102) and an embossing bottom punch (104). Top punch (102) and bottom punch (104) are configured to contact a top side (108) and a bottom side (110), respectively, of an anvil blank (106) positioned between punches (102, 104) for forming pockets (70) in top side (108) of anvil blank (106). In the present version, top and bottom punches (102, 104) are configured to strike (i.e., impact) and thereby plastically deform respective top and bottom sides (108, 110) of anvil blank (106) simultaneously. In other versions, top and bottom punches (102, 104) may be configured to plastically deform respective top and bottom sides (108, 110) sequentially.

Anvil blank (106) of the present example is in the form of a flat, rectangular metal plate, which may have already been subject to one or more preliminary machining steps, such formation (e.g., by stamping) of knife slot (66) and/or jaw alignment dimple (68) (see FIGS. 3-4). In some versions, jaw alignment dimple (68) may be formed simultaneously with pockets (70) via coining assembly (100) in the manner described below. In other versions, anvil blank (106) may be alternatively shaped, such as curved rectangular or circular, for application with a variety of other types of surgical stapler anvils, for example as described in greater detail below in connection with FIGS. 9-12.

In the present version, bottom punch (104) is secured in a stationary position and top punch (102) is movable relative to bottom punch (104) for striking top side (108) of anvil blank (106) for forming pockets (70) via plastic deformation of top side (108), while bottom side (110) of anvil blank (106) is supported and plastically deformed by bottom punch (104). In other versions, anvil blank (106) may be supported by bottom punch (104) or an independent structure (not shown), and both top punch (102) and bottom punch (104) may be simultaneously or sequentially movable relative to anvil blank (106) for plastically deforming top side (108) and bottom side (110). For instance, in one such exemplary version, anvil blank (106) may rest on bottom punch (106) which remains stationary while top punch (102) completes a downward stroke toward bottom punch (106) to thereby strike top side (108) of anvil blank (106). Following initial impact of top side (108) with top punch (102), top punch (102) may be maintained in contact with top side (108) (e.g., by being held stationary or by being actuated further downwardly into top side (108) in a direction toward bottom punch (104)), while bottom punch (104) is actuated upwardly into bottom side (110) in a direction toward top punch (102).

Still in other versions, though not shown, top punch (102) and bottom punch (104) may be reoriented such that the anvil blank (106) is contacted and coined by punches (102, 104) in a non-horizontal plane, such as a vertical plane. For instance, punches (102, 104) may be movable relative to one another along a horizontal plane, such that top punch (102) operates as a first side punch and bottom punch (104) operates as a second side punch. Furthermore, it will be appreciated that the punch actuation of coining assembly (100) may be powered by a variety of suitable means readily apparent to those of ordinary skill in the art in view of the teachings herein, such as pneumatics, hydraulics, or electric motors, for example.

Figure 6:
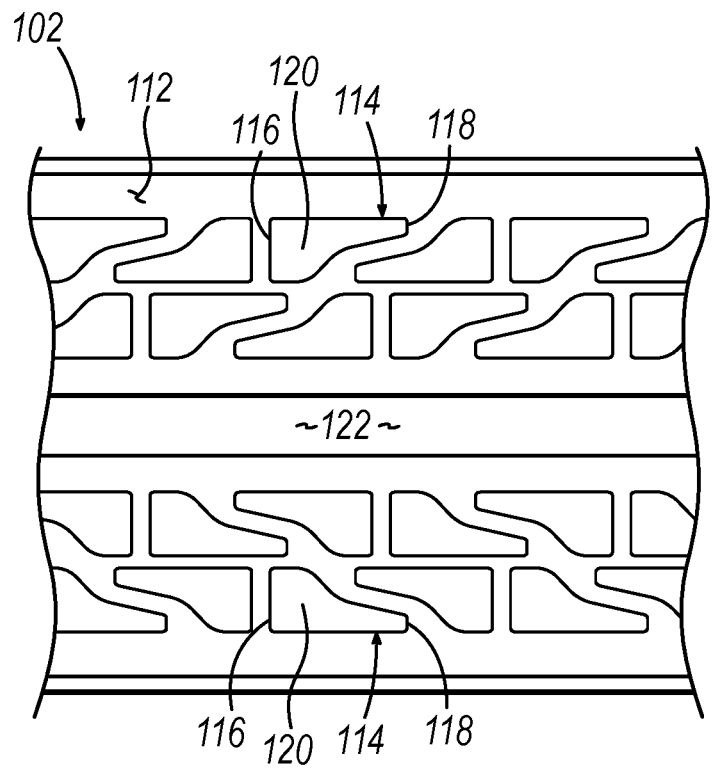
FIG. 6 depicts a schematic plan view of an underside of the pocket-forming top punch of FIG. 5.

As shown in FIG. 6, pocket-forming top punch (102) of coining assembly (100) includes a base surface (112) and a plurality of pocket forming protrusions (114) formed on base surface (112). Pocket forming protrusions (114) extend toward bottom punch (104) and are configured to directly contact and plastically deform top side (108) of anvil blank (106). In the present version, top punch protrusions (114) are suitably shaped and arranged to form anvil pockets (70) shown in FIGS. 3 and 4 described above. In particular, each top punch protrusion (114) is shaped the same and has a first end (116) that corresponds to the entry end (72) of a respective pocket (70) and has a larger first width, and a second end (118) that corresponds to the exit end (74) of the respective pocket (70) and has a smaller second width. Additionally, each top punch protrusion (114) has an elongate shape with a length that extends parallel to the length of the anvil blank (106). An outer most surface (120) of each top punch protrusion (114) may be convexly contoured to form concave base surface (78) of the respective anvil pocket (70). Accordingly, each anvil pocket (70) is ultimately formed with a shape that complements the shape of the respective top punch protrusion (114), such that each anvil pocket (70) is shaped as an inversion of the respective top punch protrusion (114). In particular, each anvil pocket (70) is formed with a generally concave shape that complements the generally convex shape of the respective top punch protrusion (114).

Top punch protrusions (114) are arranged in longitudinally adjacent pairs that exhibit reflective symmetry relative to one another such that each pair of protrusions (114) is configured to form a respective pair of pockets (70), via plastic deformation, when top punch (102) strikes top side (108) of anvil blank (106). Additionally, top punch protrusions (114) of the present example are arranged in four adjacent rows, and a recess (122) extends longitudinally through base surface (112) between the two innermost rows of protrusions (114) to account for knife slot (66) of anvil plate (62). In some versions, longitudinal recess (122) may be omitted from top punch (102). Furthermore, it will be appreciated that top punch (102) may comprise two or more pieces each having a respective base surface (112) and each having a respective one or more rows of top punch protrusions (114).

Figure 7:
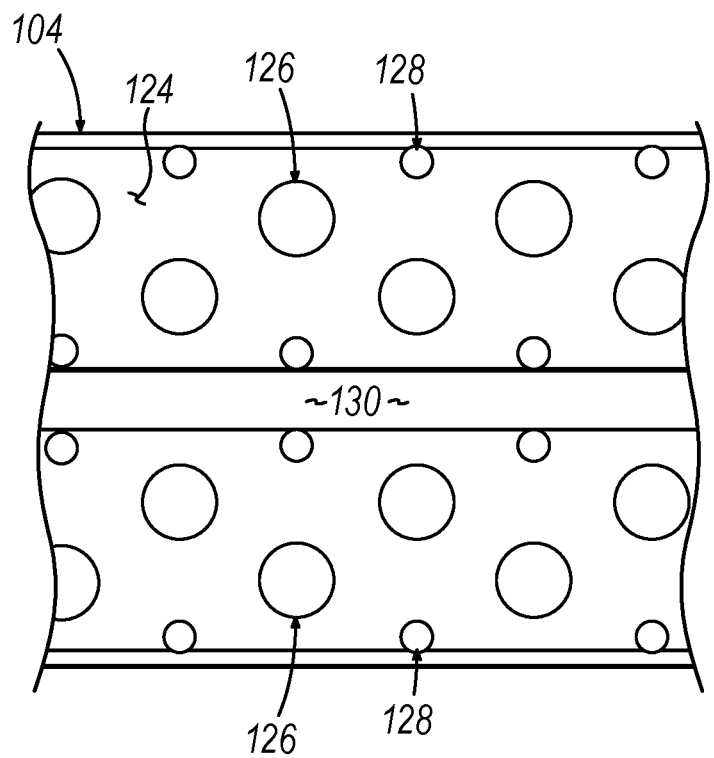
FIG. 7 depicts a schematic plan view of a top side of the embossing bottom punch of FIG. 5.

As shown schematically in FIG. 7, embossing bottom punch (104) of coining assembly (100) includes a base surface (124), a plurality of first embossing protrusions (126) formed on base surface (124), and a plurality of second embossing protrusions (128) formed on base surface (124) apart from first embossing protrusions (126). Embossing protrusions (126, 128) extend toward top punch (102) and are configured to directly contact and plastically deform bottom side (110) of anvil blank (106) while top punch protrusions (114) plastically deform top side (108) to thereby promote precise formation of anvil pockets (70). In the present example, first embossing protrusions (126) are shown in the form of convexly rounded protrusions having a first maximum dimension (e.g., a diameter) in a direction transverse to the length of bottom punch (104). Second embossing protrusions (128) are shown in the form of convexly rounded protrusions having a smaller, second maximum dimension (e.g., a diameter) in a direction transverse to the length of bottom punch (104). While embossing protrusions (126, 128) are shown in FIG. 7 as having circular profiles in the plane defined by base surface (124), it will be appreciated that embossing protrusions (126, 128) may be formed with various other suitable shapes, such as various elongate shapes or any irregular shapes, in other versions.

As shown in FIG. 7, first embossing protrusions (126) of the present version are arranged on base surface (124) of bottom punch (104) in two longitudinal rows on each side of a recess (130) that extends longitudinally along bottom punch (104). In some versions, longitudinal recess (130) may be omitted from bottom punch (104). The first embossing protrusions (126) of each row are longitudinally offset from each of the first embossing protrusions (126) of the immediately adjacent row so as to yield a longitudinal zig-zag like pattern of first embossing protrusions (126) on each side of longitudinal recess (130), as shown in FIG. 7. Additionally, second embossing protrusions (128) of the present version are arranged on base surface (124) in two longitudinal rows on each side of longitudinal recess (130) such that the two rows of first embossing protrusions (126) on each side of longitudinal recess (130) are laterally offset from and disposed between the corresponding two rows of second embossing protrusions (128). In other words, each row of second embossing protrusions (128) extends longitudinally along a respective outermost edge of bottom punch (104), or longitudinally along a respective edge of longitudinal recess (122). The second embossing protrusions (128) of each row are longitudinally offset from each of the second embossing protrusions (128) of the other row located on the same side of longitudinal recess (130). As seen in FIG. 7, first and second embossing protrusions (126, 128) are arranged relative to one another such that each first embossing protrusion (126) is longitudinally aligned with a respective second embossing protrusion (128) on the same side of longitudinal recess (130). Additionally, each such pair of first and second embossing protrusions (126, 128) is longitudinally aligned with a respective pair of first and second embossing protrusions (126, 128) on the opposing side of longitudinal recess (130).

As seen by comparison of FIGS. 6 and 7, pocket forming protrusions (114), first embossing protrusions (126), and second embossing protrusions (128) of the present version each differ from one another in size and shape. In other versions, first and second embossing protrusions (126, 128) may be similar in size and shape. Additionally, in the present version, pocket forming protrusions (114) are arranged in a pattern on top punch (102) that differs from the pattern in which first and second embossing protrusions (126, 128) are arranged on bottom punch (104). Moreover, as described in greater detail below, each embossing protrusion (126, 128) of bottom punch (104) is at least partially offset from each pocket forming protrusion (114) of top punch (102) and thus is configured to assist one or more pocket forming protrusions (114) in forming a respective one or more pockets (70) in top side (108) of anvil blank (106).

In use, as described briefly above, pocket-forming top punch (102) and embossing bottom punch (104) are configured to cooperate to form staple forming pockets (70) in top side (108) of anvil blank (106) with enhanced precision and minimal tonnage. In particular, top punch (102) and bottom punch (104) of the present example simultaneously impact the top side (108) and bottom side (110) of anvil blank (106), respectively, such that top punch protrusions (114) coin anvil pockets (70) in top side (108) while bottom punch protrusions (126, 128) emboss bottom side (110), both via plastic deformation. This simultaneous plastic deformation of bottom side (110), and specifically pushing material of bottom side (110) toward top side (108) with bottom punch protrusions (126, 128) while pushing material of top side (108)

toward bottom side (110) with top punch protrusion (114), operates to support the formation of anvil pockets (70) in top side (108) with accurate sizing and minimal imperfections. In that regard, punch protrusions (114, 126, 128) are suitably arranged and punches (102, 104) are suitably aligned such that each top punch protrusion (114) cooperates with at least one first embossing protrusion (126) and at least one second embossing protrusion (128) of bottom punch (104) to form a respective anvil pocket (70) in top side (108) with optimal precision. This cooperation of top and bottom punch protrusions (114, 126, 128) yields minimal "pulldown" of the blank material that defines the sidewalls of anvil pockets (70), such that pockets (70) resemble the shape of top punch protrusions (114) as accurately as possible. In this manner, anvil pockets (70) may be formed precisely without a need to increase tonnage of coining assembly (100), thus maximizing the tooling life of top punch (102), bottom punch (104), and any related tooling components.

B. Exemplary Alternative Embossing Bottom Punch

Figure 8:
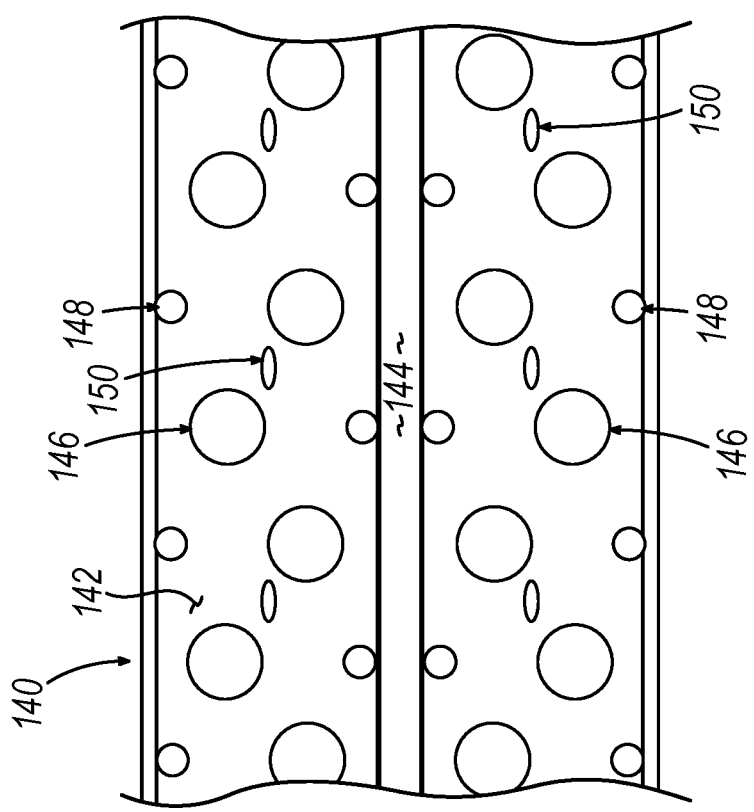
FIG. 8 depicts a schematic plan view of a portion of a top side of another exemplary embossing bottom punch configured for use with the anvil pocket coining assembly of FIG. 5.

In some instances, it may be desirable to provide embossing bottom punch (104) with an alternative configuration to further enhance the formation of anvil pockets (70) in top side (108) of anvil blank (106). FIG. 8 shows a portion of an exemplary alternative embossing bottom punch (140) configured for use with coining assembly (100) in place of bottom punch (104) described above, and which is similar to bottom punch (104) excepted as otherwise described below.

Similar to bottom punch (104), bottom punch (140) includes a base surface (142), an optional longitudinal recess (144) formed in base surface (142), and a plurality of first embossing protrusions (146) and second embossing protrusions (148) formed on base surface (142) and which are similar to embossing protrusions (126, 128) described above. Bottom punch (140) further includes a plurality of third embossing protrusions (150) shown schematically in the form of rectangular protrusions. In the present example, a row of third embossing protrusions (150) is positioned along an axis that extends longitudinally between the two rows of first embossing protrusions (146) on each lateral side of longitudinal recess (144). Furthermore, each row of third embossing protrusions (150) is configured to align with a respective longitudinal axis that extends between two longitudinal rows of pocket forming protrusions (114) on a respective lateral side of top punch (102). Accordingly, each pocket forming protrusion (114) of top punch (102) would be configured to cooperate with at least one first embossing protrusion (146), at least one second embossing protrusion (148), and at least one third embossing protrusion (150) of bottom punch (140) to form a respective anvil pocket (70) in anvil blank (106). In that regard, third embossing protrusions (150) are configured to cooperate with first and second embossing protrusions (146, 148) to enhance the precision of anvil pockets (70) formed by pocket forming protrusions (114) of top punch (102).

C. Exemplary Application to Other Surgical Stapler Types

It may be desirable to utilize versions of coining assembly (100) and the related coining methods described above to coin staple-forming pockets (70) on anvil plates of various other configurations for use with other types of surgical staplers. Such surgical staplers may be configured for use in laparoscopic or open surgeries and, by way of example only, may include any of the surgical staplers made available by Ethicon of Cincinnati, Ohio. It will be appreciated that the anvil structures described below are merely exemplary and non-limiting applications of coining assembly (100) and the related methods described above.

Figure 9:
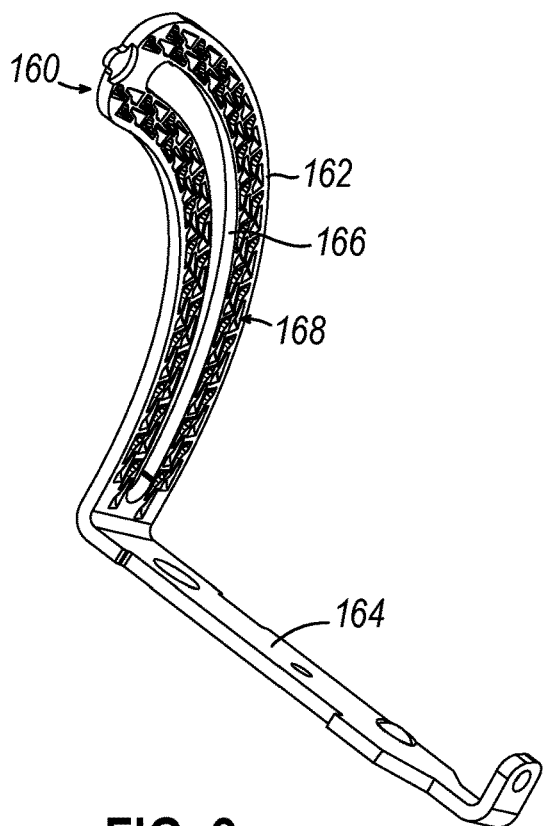
FIG. 9 depicts a perspective view of an exemplary anvil of another surgical stapler type having anvil pockets formed via a coining method similar to the method shown in FIG. 5.

FIG. 9. shows an exemplary anvil (160) configured for use with a surgical stapler (not shown) having a curved end effector as disclosed in greater detail in U.S. patent application Ser. No. 16/234,727, entitled "Surgical Stapler with Tissue Engagement Features Around Tissue Containment Pin," filed Dec. 28, 2018, issued as U.S. Pat. No. 11,202,628 on Dec. 21, 2022, the disclosure of which is incorporated by reference herein. Anvil (160) includes a curved plate portion (162) and a coupling arm (164) extending proximally from a lower end of curved plate portion (162). Curved plate portion (162) extends transversely relative to coupling arm (164) along an arcuate path and includes a curved knife slot (166) and a plurality of staple forming pockets (168) formed on a proximal side of plate portion (162) on either side of knife slot (166). Staple forming pockets (168) may be similar in shape to staple forming pockets (70) described above. It will be appreciated that top punch (102) and bottom punch (104) of coining assembly (100) may be suitably modified, for instance by arranging pocking forming protrusions (114) and embossing protrusions (126, 128) along arcuate paths, to coin staple forming pockets (168) on an anvil blank (not shown) for forming anvil (160).

Figure 10:
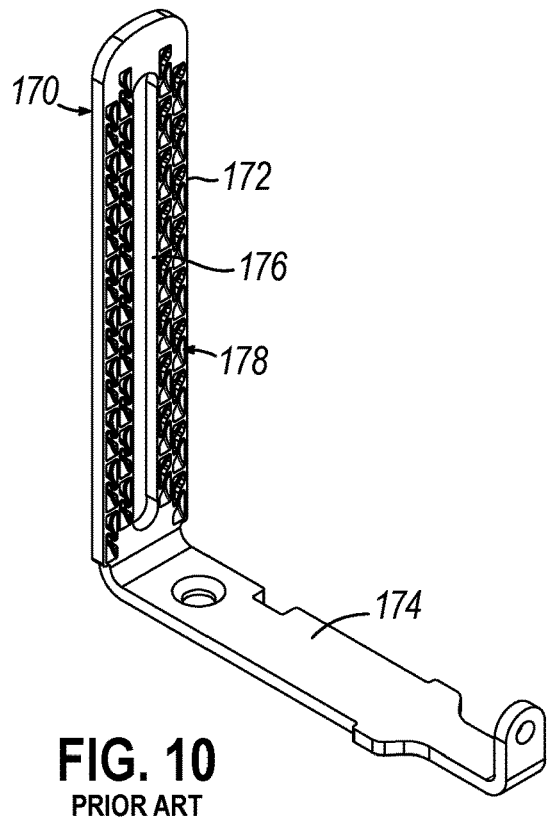
FIG. 10 depicts a perspective view of an exemplary anvil of another surgical stapler type having pockets formed via a coining method similar to the method shown in FIG. 5.

FIG. 10 shows another exemplary anvil (170) configured for use with a surgical stapler having a linear end effector as disclosed in greater detail in U.S. patent application Ser. No. 16/395,357, entitled "Tissue Cutting Washer for Right Angle Surgical Stapler," filed Apr. 26, 2019, issued as U.S. Pat. No. 11,206,403 on Mar. 8, 2022, the disclosure of which is incorporated by reference herein. Anvil (170) includes a linear plate portion (172) and a coupling arm (174) extending proximally from a lower end of curved plate portion (172). Plate portion (172) extends transversely relative to coupling arm (174) and includes a knife slot (176) and a plurality of staple forming pockets (178) formed on a proximal side of plate portion (172) on either side of knife slot (176). Staple forming pockets (178) may be similar in shape to staple forming pockets (70) described above. It will be appreciated that top punch (102) and/or bottom punch (104) of coining assembly (100) may be suitably modified as needed to coin staple forming pockets (178) on an anvil blank (not shown) for forming anvil (170).

FIG. 11 shows an exemplary anvil jaw assembly (180) of a laparoscopic surgical stapler of the type disclosed in U.S. patent application Ser. No. 16/729,553, entitled "Surgical Stapler with Toggling Distal Tip," filed Dec. 30, 2019, issued as U.S. Pat. No. 11,439,391 on Sep. 13, 2022, the disclosure of which is incorporated by reference herein. Anvil jaw assembly (180) of the present example includes a jaw (182) and an anvil plate (186) configured to be secured to an underside surface (184) of jaw (182), for example by welding or heat staking. Anvil jaw assembly (180) is configured to pivot relative to a staple cartridge (not shown) of the corresponding instrument end effector for clamping tissue. Anvil plate (186) includes a stepped anvil surface (188), a longitudinal knife slot (190), and a plurality of staple forming pockets (192) formed on stepped anvil surface (188) on either side of knife slot (190) such that the innermost rows of pockets (192) are raised relative to the outermost rows of pockets (192) in a direction away from jaw (182).

Staple forming pockets (192) of the present example are shaped to form staples with a B-like shape in which the crown and each bent leg of a formed staple lie in the same plane. In particular, each pocket (192) is generally rectangular in shape and includes a concave base surface configured to deform a respective staple leg. Pockets (192) are arranged in longitudinally adjacent pairs, each pair being longitudinally aligned and configured to form a respective staple with a B-shape. In other versions, pockets (192) may be shaped similar to pockets (70) for forming three-dimensional staples. It will be appreciated that top punch (102) and/or bottom punch (104) of coining assembly (100) may be suitably modified as needed to coin staple forming pockets (192) on a rectangular anvil blank (not shown) for forming anvil plate (186). Following formation of anvil plate (186), anvil plate (186) may be secured to jaw (182).

Figure 12:
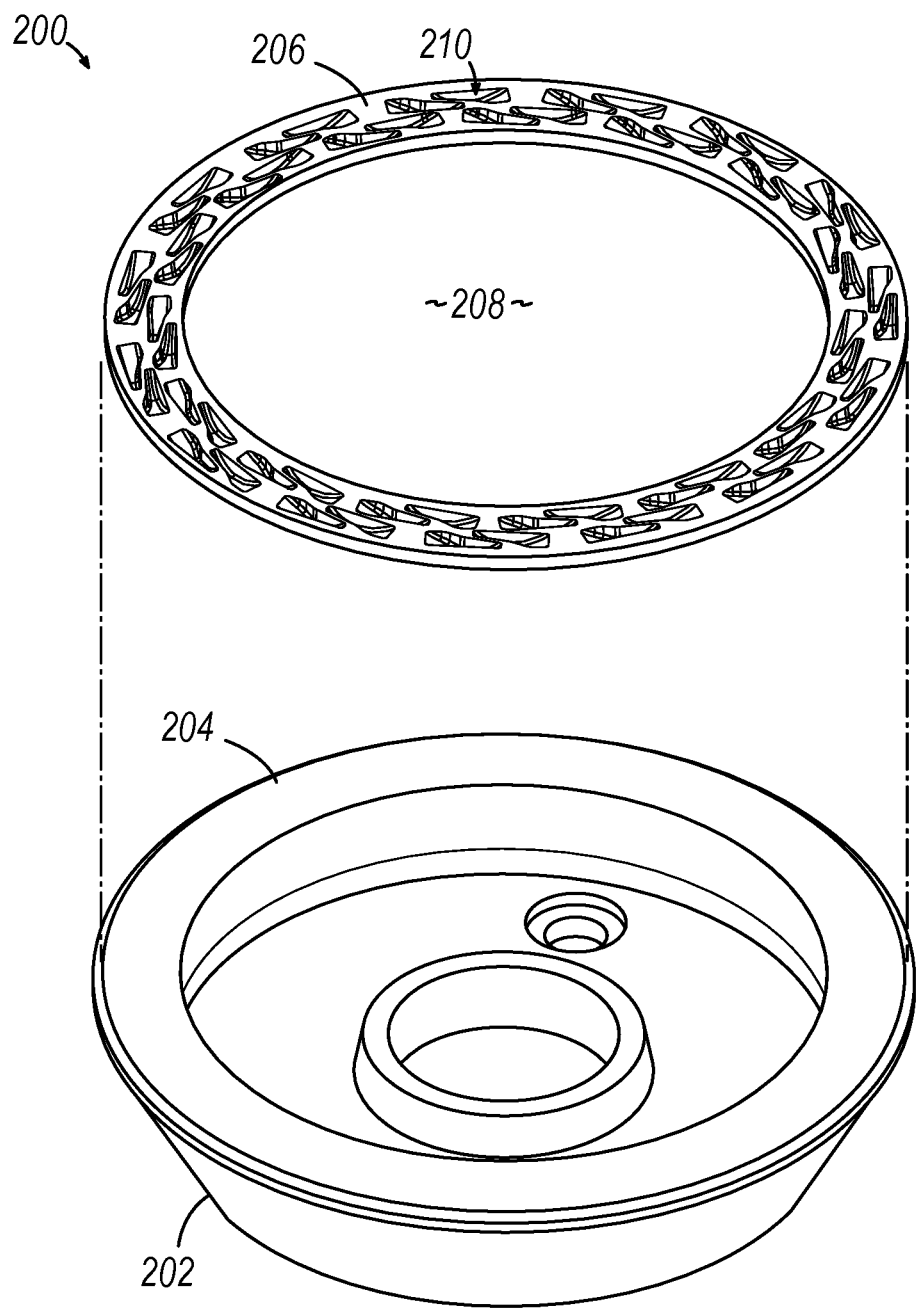
FIG. 12 depicts a disassembled perspective view of a portion of an exemplary anvil assembly of another surgical stapler type, showing an anvil plate having pockets formed via a coining method similar to the method shown in FIG. 5.

FIG. 12 shows a portion of an exemplary anvil assembly (200) of a circular surgical stapler of the type disclosed in U.S. Pat. Pub. No. 2017/0258471, entitled "Methods and Systems for Performing Circular Stapling," published Sep. 14, 2017, or U.S. Pat. Pub. No. 2020/0113565, entitled "Latch to Prevent Back-driving of Circular Surgical Stapler," published Apr. 16, 2020, the disclosures of which are incorporated by reference herein. Anvil assembly (200) includes a circular base cap (202) and an annular anvil plate (206) configured to secured to a proximal face (204) of base cap (202), for example by welding. Annular anvil plate (206) includes a circular central opening (208) configured to receive a cylindrical knife member (not shown) therethrough. A proximal side of anvil plate (206) includes a pair of concentric annular arrays of staple forming pockets (210). Pockets (210) may be shaped similar to pockets (70) for forming three-dimensional staples, or alternatively for forming staples having a B-shape, as described in greater detail above in connection with FIG. 4. It will be appreciated that top punch (102) and bottom punch (104) of coining assembly (100) may be suitably modified as needed, for instance by arranging punch protrusions (114, 126, 128) in annular arrays, to coin staple forming pockets (210) on a circular anvil blank (not shown) for forming anvil plate (186). Following formation of anvil plate (206), anvil plate (206) may be secured to base cap (202).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of forming an anvil for a surgical stapler with a first punch having a first plurality of protrusions and a second punch opposed from the first punch and having a second plurality of protrusions, the method comprising: (a) positioning a workpiece between the first punch and the second punch; (b) contacting a first side of the workpiece with the first punch and thereby plastically deforming the first side with the first plurality of protrusions to displace at least some material of the first side in a direction toward a second side of the workpiece; (c) while contacting the first side of the workpiece with the first punch, contacting the second side of the workpiece with the second punch and thereby plastically deforming the second side with the second plurality of protrusions to displace at least some material of the second side in a direction toward the first side; and (d) forming a plurality of pockets in the first side via the contact of the first punch with the first side and the simultaneous contact of the second punch with the second side, wherein each pocket is configured to deform a leg of a surgical staple.

Example 2

The method of Example 1, wherein each of the pockets includes a concave base surface configured to deform a leg of a staple.

Example 3

The method of any of the preceding Examples, wherein each protrusion of the first plurality of protrusions is shaped differently than each protrusion of the second plurality of protrusions.

Example 4

The method of any of the preceding Examples, wherein each protrusion of the first plurality of protrusions is of a first type, wherein at least some protrusions of the second plurality of protrusions are of a second type that differs from the first type in at least one of shape or size.

Example 5

The method of Example 4, wherein at least some protrusions the second plurality of protrusions are of a third type that differs from each of the first type and the second type in at least one of shape or size.

Example 6

The method of any of the preceding Examples, wherein at least some protrusions of the first plurality of protrusions have a maximum dimension extending in a first direction, wherein at least some protrusions of the second plurality of protrusions have a maximum dimension extending in a second direction transverse to the first direction.

Example 7

The method of any of the preceding Examples, wherein the first plurality of protrusions is arranged in a first configuration, wherein the second plurality of protrusions is arranged in a second configuration different than the first configuration.

Example 8

The method of any of the preceding Examples, wherein each protrusion of the first plurality of protrusions has a first longitudinal end having a first width and a second longitudinal end having a second width different than the first width.

Example 9

The method of any of the preceding Examples, wherein the first punch comprises a top punch and the second punch comprises a bottom punch, wherein the first side of the workpiece comprises a top side and the second side of the workpiece comprises a bottom side.

Example 10

The method of any of the preceding Examples, wherein each of the pockets has a shape that complements a shape of a respective protrusion of the first plurality of protrusions.

Example 11

The method of any of the preceding Examples, wherein each of the pockets has an elongate shape with a first end portion, a second end portion, and a medial portion therebetween, wherein the first end portion is configured to guide a staple leg in an unformed state toward the medial portion, wherein the second end portion is configured to guide the staple leg in a deformed state away from the medial portion.

Example 12

The method of any of the preceding Examples, wherein forming the plurality of pockets in the first side comprises forming the pockets such that at least one pocket is separated from an adjacent pocket by a wall having a thickness of less than or equal to 0.010 inches.

Example 13

The method of any of the preceding Examples, wherein the workpiece is flat, wherein the workpiece is also rectangular or circular in shape.

Example 14

The method of any of the preceding Examples, wherein the workpiece includes an elongate slot, wherein forming the plurality of pockets in the first side of the workpiece comprises forming a first plurality of pockets on a first side of the elongate slot and forming a second plurality of pockets on a second side of the elongate slot.

Example 15

The method of any of the preceding Examples, further comprising coupling the anvil having the pockets to a portion of a surgical stapler end effector.

Example 16

A method of forming an anvil for a surgical stapler with a top punch having a first plurality of protrusions and a bottom punch having a second plurality of protrusions, the method comprising: (a) positioning a workpiece between the top punch and the bottom punch such that a top side of the workpiece faces the top punch and a bottom side of the workpiece faces the bottom punch; (b) contacting a top side of the workpiece with the first punch and thereby plastically deforming the top side with the first plurality of protrusions; (c) while contacting the top side of the workpiece with the top punch, engaging a bottom side of the workpiece with the bottom punch and thereby plastically deforming the bottom side with the second plurality of protrusions; (d) forming a plurality of pockets in the top side via the contact of the top punch with the top side and the simultaneous contact of the bottom punch with the bottom side, wherein each of the pockets has a shape that complements a shape of a respective protrusion of the first plurality of protrusions; and (e) after forming the pockets in the top side of the workpiece, coupling the workpiece to a portion of a surgical stapler end effector.

Example 17

The method of Example 16, wherein each protrusion of the first plurality of protrusions is shaped differently than each protrusion of the second plurality of protrusions.

Example 18

The method of any of Examples 16 through 17, wherein the first plurality of protrusions is arranged in a first configuration, wherein the second plurality of protrusions is arranged in a second configuration different than the first configuration.

Example 19

A method of forming an anvil for a surgical stapler with a movable first punch having a first plurality of protrusions and a stationary second punch opposed from the first punch and having a second plurality of protrusions, the method comprising: (a) supporting the workpiece with the second punch; (b) advancing the first punch toward the second punch while the second punch remains stationary; (c) contacting a first side of the workpiece with the first punch and thereby plastically deforming the first side with the first plurality of protrusions; (d) while contacting the first side of the workpiece with the first punch, engaging a second side of the workpiece with the second punch and thereby plastically deforming the second side with the second plurality of protrusions; (e) forming a plurality of pockets in the first side via the contact of the first punch with the first side and the simultaneous contact of the second punch with the second side; and (f) after forming the pockets in the top side of the workpiece, coupling the workpiece to a portion of a surgical stapler end effector.

Example 20

The method of Example 19, wherein the first punch comprises a top punch and the second punch comprises a bottom punch, wherein the first side of the workpiece comprises a top side and the second side of the workpiece comprises a bottom side.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A method of forming an anvil for a surgical stapler with a first punch having a first plurality of protrusions and a second punch opposed from the first punch and having a second plurality of protrusions, the method comprising:
   (a) positioning a workpiece between the first punch and the second punch;
   (b) contacting a first side of the workpiece with the first punch and thereby plastically deforming the first side with the first plurality of protrusions to displace at least some material of the first side in a direction toward a second side of the workpiece;
   (c) while contacting the first side of the workpiece with the first punch, contacting the second side of the workpiece with the second punch and thereby plastically deforming the second side with the second plurality of protrusions to displace at least some material of the second side in a direction toward the first side; and
   (d) forming a plurality of pockets in the first side via the contact of the first punch with the first side and the simultaneous contact of the second punch with the second side, wherein each pocket is configured to deform a leg of a surgical staple,
   wherein each protrusion of the first plurality of protrusions is of a first type, wherein at least some protrusions of the second plurality of protrusions are of a second type that differs from the first type in at least one of shape or size.

2. The method of claim 1, wherein each of the pockets includes a concave base surface configured to deform a leg of a staple.

3. The method of claim 1, wherein each protrusion of the first plurality of protrusions is shaped differently than each protrusion of the second plurality of protrusions.

4. The method of claim 1, wherein at least some protrusions of the second plurality of protrusions are of a third type that differs from each of the first type and the second type in at least one of shape or size.

5. The method of claim 1, wherein at least some protrusions of the first plurality of protrusions have a maximum dimension extending in a first direction, wherein at least some protrusions of the second plurality of protrusions have a maximum dimension extending in a second direction transverse to the first direction.

6. The method of claim 1, wherein the first plurality of protrusions is arranged in a first configuration, wherein the second plurality of protrusions is arranged in a second configuration different than the first configuration.

7. The method of claim 1, wherein each protrusion of the first plurality of protrusions has a first longitudinal end having a first width and a second longitudinal end having a second width different than the first width.

8. The method of claim 1, wherein the first punch comprises a top punch and the second punch comprises a bottom punch, wherein the first side of the workpiece comprises a top side and the second side of the workpiece comprises a bottom side.

9. The method of claim 1, wherein each of the pockets has a shape that complements a shape of a respective protrusion of the first plurality of protrusions.

10. The method of claim 1, wherein each of the pockets has an elongate shape with a first end portion, a second end portion, and a medial portion therebetween, wherein the first end portion is configured to guide a staple leg in an unformed state toward the medial portion, wherein the second end portion is configured to guide the staple leg in a deformed state away from the medial portion.

11. The method of claim 1, wherein forming the plurality of pockets in the first side comprises forming the pockets such that at least one pocket is separated from an adjacent pocket by a wall having a thickness of less than or equal to 0.010 inches.

12. The method of claim 1, wherein the workpiece is flat, wherein the workpiece is also rectangular or circular in shape.

13. The method of claim 1, wherein the workpiece includes an elongate slot, wherein forming the plurality of pockets in the first side of the workpiece comprises forming a first plurality of pockets on a first side of the elongate slot and forming a second plurality of pockets on a second side of the elongate slot.

14. The method of claim 1, further comprising coupling the anvil having the pockets to a portion of a surgical stapler end effector.

\* \* \* \* \*